(12) United States Patent
Simmons et al.

(10) Patent No.: US 11,058,808 B2
(45) Date of Patent: Jul. 13, 2021

(54) PRESSURE SYSTEM WITH ABSOLUTE PRESSURE SENSOR

(71) Applicant: MEDELA HOLDING AG, Baar (CH)

(72) Inventors: Bryan D. Simmons, North Aurora, IL (US); John R. Skach, Cary, IL (US); David Cho, Arlington Heights, IL (US)

(73) Assignee: MEDELA HOLDING AG, Baar (CH)

(*) Notice: Subject to any disclaimer, the term of this patent is extended or adjusted under 35 U.S.C. 154(b) by 191 days.

(21) Appl. No.: 15/096,720

(22) Filed: Apr. 12, 2016

(65) Prior Publication Data

US 2016/0296680 A1    Oct. 13, 2016

Related U.S. Application Data

(60) Provisional application No. 62/146,596, filed on Apr. 13, 2015.

(51) Int. Cl.
*A61M 1/06* (2006.01)
*A61M 1/00* (2006.01)

(52) U.S. Cl.
CPC ............ *A61M 1/06* (2013.01); *A61M 1/0031* (2013.01); *A61M 2205/3358* (2013.01); *A61M 2205/3584* (2013.01); *A61M 2205/50* (2013.01); *A61M 2205/52* (2013.01)

(58) Field of Classification Search
CPC ........ A61M 1/0031; A61M 2205/3358; A61M 1/06; A61M 1/062; A61M 1/064; A61M 1/0037; A61M 2205/50; A61M 2205/52; A61M 1/0066
See application file for complete search history.

(56) References Cited

U.S. PATENT DOCUMENTS

| | | | | |
|---|---|---|---|---|
| 5,215,450 A | * | 6/1993 | Tamari | A61M 1/0031 138/119 |
| 6,629,525 B2 | * | 10/2003 | Hill | A61M 16/10 128/202.26 |
| 2006/0122558 A1 | * | 6/2006 | Sherman | A61M 1/0031 604/67 |
| 2006/0266357 A1 | * | 11/2006 | McCombs | A61M 16/10 128/204.26 |

(Continued)

FOREIGN PATENT DOCUMENTS

| | | |
|---|---|---|
| CN | 104162219 A | 11/2014 |
| EP | 1619121 A1 | 1/2006 |

(Continued)

OTHER PUBLICATIONS

International Search Report and Written Opinion, International Application No. PCT/IB2016/000810, dated Nov. 10, 2016.

(Continued)

*Primary Examiner* — Scott J Medway
(74) *Attorney, Agent, or Firm* — Marshall, Gerstein & Borun LLP (57) ABSTRACT

A pressure system in a communication loop with an atmospheric pressure data source is set forth. Atmospheric pressure data from the atmospheric pressure data source can be received by a processor to set one or more operating parameters for the pressure system based on environmental data provided in the atmospheric pressure data from an absolute pressure sensor or other atmospheric data source.

6 Claims, 4 Drawing Sheets

(56) References Cited

U.S. PATENT DOCUMENTS

| | | | | |
|---|---|---|---|---|
| 2006/0283450 | A1* | 12/2006 | Shissler | A61B 5/4836 128/204.21 |
| 2008/0009815 | A1* | 1/2008 | Grabenkort | A61M 1/0031 604/346 |
| 2008/0041401 | A1* | 2/2008 | Casola | A61M 1/0031 128/897 |
| 2008/0071216 | A1* | 3/2008 | Locke | A61M 1/0027 604/119 |
| 2008/0125697 | A1* | 5/2008 | Gao | A61M 1/0031 604/35 |
| 2009/0099511 | A1* | 4/2009 | Sutrina | A61M 1/06 604/74 |
| 2009/0326488 | A1* | 12/2009 | Budig | A61M 1/0001 604/319 |
| 2010/0016767 | A1* | 1/2010 | Jones | A61M 1/0088 601/10 |
| 2010/0168867 | A1* | 7/2010 | Swain | A61M 5/16881 623/23.49 |
| 2010/0280422 | A1* | 11/2010 | Hartwell | A61M 1/0031 601/6 |
| 2011/0114094 | A1* | 5/2011 | Stone | A61M 16/12 128/204.22 |
| 2012/0035543 | A1* | 2/2012 | Kamen | A61M 5/14244 604/113 |
| 2012/0316799 | A1* | 12/2012 | Gagel | A61M 1/1658 702/50 |
| 2015/0020807 | A1* | 1/2015 | Kimmel | A61M 16/0875 128/204.21 |
| 2016/0091309 | A1* | 3/2016 | Sasaki | G01C 5/06 73/384 |
| 2016/0287767 | A1* | 10/2016 | Simmons | A61M 1/06 |
| 2017/0072118 | A1* | 3/2017 | Makower | A61M 1/06 |
| 2018/0311419 | A1* | 11/2018 | Locke | H01H 35/346 |
| 2020/0078503 | A1* | 3/2020 | Bartlett | A61M 1/062 |

FOREIGN PATENT DOCUMENTS

| | | | | |
|---|---|---|---|---|
| EP | | 2412392 A1 | 2/2012 | |
| EP | | 2803379 A1 | 11/2014 | |
| NL | WO 2015014643 A1 * | | 2/2015 | A61M 1/06 |
| TW | | 201028183 A | 8/2010 | |
| WO | WO-00/66195 A1 | | 11/2000 | |
| WO | WO-2008/008781 A2 | | 1/2008 | |

OTHER PUBLICATIONS

European Patent Application No. 16730479.9, Communication Pursuant to Article 94(3) EPC, dated Jul. 18, 2018.
European Patent Application No. 16730479.9, Summons to Attend Oral Proceedings Pursuant to Rule 115(1) EPC, dated Sep. 27, 2019.
Chinese Patent Application No. 201680029808X, First Office Action and Search Report, dated Nov. 28, 2019.

* cited by examiner

PRESSURE SYSTEM WITH ABSOLUTE PRESSURE SENSOR

CROSS-REFERENCE TO RELATED APPLICATIONS

This application claims benefit of the filing date of U.S. Provisional Patent Application No. 62/146,596 (filed Apr. 13, 2015 and entitled "PRESSURE SYSTEM WITH ABSOLUTE PRESSURE SENSOR"), the disclosure of which is hereby incorporated by reference in its entirety.

FIELD OF THE DISCLOSURE

The present disclosure relates generally to an absolute pressure sensor in a pressure system. More particularly, the disclosure relates to the setting of operating parameters of the pressure system using environmental information obtained from a suitable source, such as an absolute pressure sensor.

BACKGROUND

Differential pressure sensors are routinely employed to sense information used for operating pressure systems. For example, breastmilk expression systems can utilize one or more pressure sources. Typically, these pressure sources can include vacuum generators, hydraulic sources, or any other suitable pressure source that cyclically applies pressure to a breast or the breasts of a user. Vacuum sources can include a volume displacing mechanism to generate pressure. For instance, diaphragm pumps can include a membrane to generate pressure, whereas a piston-barrel assembly can include a plunger-end of a piston to generate pressure. Other pressure systems and breastmilk expression systems exist as well.

Some known breastmilk expression systems are closed pressure systems. Such systems typically open to ambient air by using, for example, a solenoid valve when a controller indicates that an adjustment to the pressure in the system is needed. One drawback associated with using differential pressure sensors to provide pressure information in breastmilk expression systems is that information available for operation of the system is limited to the capabilities of the pressure sensing components present in the system. Another drawback, at least in the case of solenoid valves, is the need to supply power to the valve.

Pressure systems can function differently under different environmental conditions. Environmental conditions at the location of the consumer may differ from environmental conditions where pressure delivery devices are constructed, assembled, shipped, rented, or purchased. Further, the consumer may travel to locations where varied environmental conditions, due to elevation or weather, can affect performance of the system. Therefore, it is desirable to provide a system that can account for changes in environmental conditions without the added cost of one or more additional components to obtain the needed environmental information.

SUMMARY OF THE DISCLOSURE

In accordance with the principles of the present disclosure, an improved pressure system can be configured to obtain environmental information related to environmental conditions surrounding the system, such as atmospheric pressure, without adding the expense of one or more additional absolute pressure sensors, or switches, or other components. In an exemplary embodiment, atmospheric pressure data can be provided to a controller of the pressure system.

For example, atmospheric pressure data sources can supply atmospheric pressure data from a measured pressure as detected by an absolute pressure sensor in, or connectable to, the system. Atmospheric pressure data sources can also include a number entered into a controller associated with the pressure system, or other environmental information entered by a user, such as a number derived from a table containing information relevant to the local environmental conditions surrounding the pump, a number obtained from or detected by an associated electronic device connectable to the system, or any other suitable source of atmospheric pressure or environmental condition data delivered to, retrieved from, or input by a suitable source or user as an input to the pressure system.

The controller, or other suitable connectable device, can process the atmospheric pressure data to set one or more operating parameters of the pressure system. The pressure system may include a vacuum, hydraulic circuit, or any other suitable pressure system.

In the case of a pressure system having a vacuum, information from the atmospheric pressure data source can be processed to set one or more operating parameters of the system. For example, in an embodiment an atmospheric pressure data source can be used in a breastmilk expression system to determine the limits of capability of the pump, or to modify operation of the pump to adapt to changing environmental conditions. Once operation parameter(s) are processed, the pressure system may be operated within, i.e., in compliance with, the parameter(s).

In an exemplary embodiment, additional advantages can be achieved in a pressure system connected, directly or indirectly, to an absolute pressure sensor. Specifically, the system can be configured to obtain atmospheric pressure data, as desired, from the absolute pressure sensor to continually or intermittently monitor performance levels of the system while environmental conditions are possibly changing during operation or between operations of the system.

In an embodiment data from the absolute pressure sensor can be used by the system to control relative pressure in a pressure system, such as a breastmilk expression system, by accounting for the initial atmospheric pressure. In other words, data from the same absolute pressure sensor can be used to both determine atmospheric pressure and control pressure within the breastmilk expression system. Data from the absolute pressure sensor can be used by the breastmilk expression system controller continuously, nearly-continuously, or at regular, irregular, or random intervals, to provide information to a controller or associated controller. The data can then be compared, if desired, or otherwise incorporated into an ideal or model pressure-versus-time curve to a desired pressure profile for the pressure system.

In accordance with the principles of the present disclosure, a discrepancy, or deviation, between the actual measured pressure delivered by the pressure system at a given time interval from initiation of the pressure system, can be identified using the atmospheric pressure data as an input, or calculated factor, by a processor or microprocessor associated with the controller, or in wireless or hardwired communication with the controller. The controller can then respond, or take an action, based on the discrepancy, to either make adjustments in the control of the pressure system, and/or to provide feedback to a user of the system.

Thus, if a discrepancy is determined between the absolute pressure data from an absolute pressure sensor and the expected system pressure at any given point, the pressure system can be adjusted accordingly. For example, if the pressure system is a breastmilk expression system including a volume displacing mechanism, then the controller can initiate a signal to change the displacement of the volume displacing mechanism to bring the pressure in the system to the expected level and remove the discrepancy. Alternatively, the controller can initiate a feedback signal warning or informing a user of the discrepancy. Additionally, the controller can further warn the user regarding the magnitude of the discrepancy, and whether any user action is needed, if desired, in a pressure system, constructed in accordance with the principles herein.

Given the example above, when the controller initiates the signal to adjust the pressure in the system, the signal can be initiated in any suitable way, such as via an actuator associated with the volume displacing mechanism, to increase or decrease the driving force supplied to the volume displacing mechanism. The signal generated by the controller to change the pressure of the exemplary system might also be applied to increase or decrease the current delivered to one or more components of the exemplary system supplied to a motor in communication with the volume displacing mechanism of the exemplary pressure system.

In an exemplary embodiment constructed in accordance with the principles herein, where a discrepancy exists between the actual measured pressure delivered by the pressure source and the model pressure-versus-time curve at a given time, or during a given duration or interval, or a pattern of discrepancies is determined for a series of different times or time intervals following initiation of a stroke or commencement of a pressure cycle of a pressure system, the discrepancies may be indicative of a leak or other condition not correctable by making adjustments in the system. Even if the condition is correctable, the condition may be one for which a feedback signal indicating that user attention is nonetheless recommended, can help avoid unnecessary strain on the pressure system or other potentially detrimental consequences.

For example, in a breastmilk expression system constructed in accordance with the principles herein, a series or pattern of discrepancies in expected pressure levels for a period of time may be indicative of a user not having correctly arranged one or both breastshield assemblies, disconnection of a length of tubing in a pressure circuit, undesired liquid in the circuit, or some other air leak, malfunction, or problem in need of attention. Firmware associated with the processor or microprocessor of the controller or connected or stored software can, upon identification of such conditions, provide a feedback signal to a user interface to notify the user of the condition. The feedback signal may be a visual indication displayed on a user interface panel, such as a solid or flashing light or message, an audible signal such as a beeping sound or other alarm, a tactile signal such as vibration of a component of the breastmilk expression system such as a housing for the vacuum source, or of a smartphone, notebook computer, tablet, phablet, GPS (Global Positioning System) or GPS-enabled device, printer, smart watch, smart glasses, smart bracelet, wearable electronic device, PDA (personal digital assistant), pager, computing device configured for wireless communication, or the like that is in wireless and/or wired communication with the breastmilk expression system. Instead or in addition, the controller or associated connectable devices could include programming to cause the controller to return the pressure system to a specified position, such as an initial position, upon identification of particular conditions.

In accordance with the principles herein, environmental data can be retrieved using one or more atmospheric pressure data sources. In an embodiment where the source is associated with a breastmilk expression system, the system can be configured to be interrogated to supply atmospheric pressure data based on an altitude or geographic position of the device, or any other suitable environmental condition input can be input to the system from an associated device selectively connected to the controller.

An altimeter or a global positioning satellite (GPS)-based geographic position sensor are examples of sources of altitude or geographic position information that could be used as a data point from which to identify atmospheric pressure data such as from a look-up table or database. To conserve memory requirements, the look-up table or database may be stored remotely from the pressure system, such as on an internet cloud-based server. By way of particular examples, the pressure system may, wirelessly or via a data communication cord or some combination thereof, communicate with a personal computing device such as a smartphone, notebook computer, tablet, phablet, GPS (Global Positioning System) or GPS-enabled device, printer, smart watch, smart glasses, smart bracelet, wearable electronic device, PDA (personal digital assistant), pager, computing device configured for wireless communication, or the like having an absolute pressure sensor, an altimeter or a geographic position sensor (or a software application installed thereon that employs data from the personal computing device, or from the pressure system, to derive altitude or geographic position) that serves as the source of geographic position information, and/or has a compatible software application installed thereon that, locally or via one or more of cellular telephone network, satellite transmission, cable television network, or internet communication, or some combination thereof, communicates with a remote server or website, at which a look-up table or database is interrogated or otherwise determines and provides data indicative of atmospheric pressure at the location of the breastmilk expression system.

Absolute pressure data inherently incorporates measurement of atmospheric pressure. Supplying data to a pressure system indicative of initial absolute pressure can allow the system to be adjusted, as needed, to perform as best as possible under the current environmental conditions.

For example, if the pressure system is a breastmilk expression system, absolute pressure data can be considered in the system setup to maximize available performance of the system before the initiation of a pumping session. Based on the absolute pressure data, one or more operating parameters of the breastmilk expression system can be adjusted by the system, if possible. Thus, operation of the exemplary pressure system at different altitudes and/or geographic positions can be tailored, where possible, to optimize performance of the pressure system under given environmental conditions.

A pressure system constructed in accordance with the principles herein can include a pressure circuit selectively connected to a pressure system. An atmospheric pressure element can be provided in communication with the pressure circuit of the pressure system. One or more operating parameters for the pressure system can be controllable based on a circuit, or loop, or other suitable software or hardware that limits operation based on a reading from the atmospheric pressure element that is received by the circuit. The pressure system can further include a pressure source. The pressure circuit can connect the pressure source to a breastshield assembly of the pressure system. The pressure system can include a pressure source that is a positive pressure source. The pressure system can include a pressure source that is a negative pressure source.

In an embodiment, the pressure system can further include a circuit, or loop, or other suitable software or hardware for setting a peak negative pressure based the reading. The pressure system can include an atmospheric pressure element such as an absolute pressure sensor connected either directly or indirectly to the pressure circuit.

Another embodiment of a pressure system including a pressure source can include a system formed of hardware, software, or a combination of hardware and software for one or more of the following: establishing, controlling, and retrieving one or more operating parameters for the pressure system based on atmospheric pressure data for the pressure system. The system can selectively expose the pressure circuit to ambient air, and an absolute pressure sensor can be connected to the pressure circuit to provide the initial atmospheric pressure data. The absolute pressure sensor can form a data sensing communication loop with a controller of the pressure source through which absolute pressure data transmits to the controller. The controller can include a program stored on a non-transitory computer readable medium, or circuit, or loop, or other suitable software or hardware. The program can include instructions responsive to the absolute pressure data. The pressure system can include any suitable cyclic pressure system, such as a breastmilk expression system where the pressure source includes a reciprocating volume displacing mechanism disposed in a chamber. An interior of the chamber can be in communication with a breastshield assembly of the breastmilk expression device.

An embodiment of a method of manufacturing a pressure system is set forth. The method can include providing an atmospheric pressure data source connectable to a pressure circuit of the pressure system. A processor in operable communication with the pressure system can also be provided. The processor can be configured to receive atmospheric pressure data from the atmospheric pressure data source. The processor in the method can be configured to determine a peak pressure level for operating the pressure system using the atmospheric pressure data.

In an embodiment, atmospheric pressure data can be obtained repeatedly for the pressure system via an absolute pressure sensor. The pressure system can be configured to deliver a non-uniform pressure curve during a cycle.

An exemplary method for initializing a pressure source of a breastmilk expression system in accordance with the principles herein can include: selectively placing a pneumatic circuit of the breastmilk expression system in communication with ambient air; identifying atmospheric pressure within the pneumatic circuit of the breastpump; and setting a peak available pressure based on the identified atmospheric pressure. The method can include identifying atmospheric pressure within the pneumatic circuit of the breastmilk expression system by measuring absolute pressure using an absolute pressure sensor.

According to the present disclosure, no more than one absolute pressure sensor is required to be used in the pressure system.

Yet another embodiment constructed in accordance with the principles herein can include a breastmilk expression system having a pressure source. A breastshield assembly can be provided in fluid communication with the pressure source. An absolute pressure sensor can be provided in fluid communication with the pressure source and the breastshield assembly. The absolute pressure sensor can be in selective communication with an outlet exposing the absolute pressure sensor to ambient pressure.

The present invention may include a pressure circuit selectively connected to a pressure system with an atmospheric pressure element in communication with the pressure circuit of the pressure system and one or more operating parameters for the pressure system controllable based on a circuit that adjusts or limits, if desired, operation based on a reading from the atmospheric pressure element that is received by the circuit. The pressure system may further include a pressure source, the pressure circuit connecting the pressure source to a breastshield assembly of the pressure system. The pressure source is a positive pressure source. Alternately, the pressure source may be a negative pressure source. The pressure system may include a circuit for setting a peak negative pressure based the reading. The atmospheric pressure element may be an absolute pressure sensor connected at least one of directly and indirectly to the pressure circuit.

A pressure system of the present disclosure may include a system for at least one of establishing, controlling, and retrieving one or more operating parameters for the pressure system based on atmospheric pressure data for the pressure system including a pressure source that selectively exposes the pressure circuit to ambient air, and an absolute pressure sensor connected to the pressure circuit, the absolute pressure sensor forming a data sensing communication loop with a controller of the pressure source through which absolute pressure data transmits to the controller. The pressure system may be one in which the controller includes a program stored on a non-transitory computer readable medium, the program including instructions responsive to the absolute pressure data.

The pressure system may be further defined by a breastmilk expression system wherein the pressure source includes a reciprocating volume displacing mechanism disposed in a chamber. An interior of the chamber may be in communication with the breastshield assembly.

A method of manufacturing a pressure system is also disclosed, including providing an atmospheric pressure data source connectable to a pressure circuit of the pressure system; and providing a processor in operable communication with the pressure system, the processor configured to receive atmospheric pressure data from the atmospheric pressure data source.

According to the method of manufacturing a pressure system of the present disclosure, the processor may be configured to determine a peak pressure level for operating the pressure system using the atmospheric pressure data. The atmospheric pressure data can be obtained repeatedly for the pressure system via an absolute pressure sensor. The pressure system may be configured to deliver a non-uniform pressure curve during a cycle.

A method for initializing a pressure source of a breastmilk expression system is also disclosed, including selectively placing a pneumatic circuit of the breastmilk expression system in communication with ambient air; identifying atmospheric pressure within the pneumatic circuit of the breastpump; and setting a peak available pressure based on the identified atmospheric pressure. Identifying atmospheric pressure within the pneumatic circuit of the breastmilk expression system may include measuring absolute pressure using an absolute pressure sensor.

A breastmilk expression system of the present disclosure can include a pressure source; a breastshield assembly in fluid communication with the pressure source; and an absolute pressure sensor in fluid communication with the pressure source and the breastshield assembly, the absolute pressure sensor being in selective communication with an outlet exposing the absolute pressure sensor to ambient pressure. The breastmilk expression system may additionally include an operating parameter decision loop, operably connected to the absolute pressure sensor, and controlling the operation of the breastmilk expression system based on information obtained from the absolute pressure sensor.

The operating parameter decision loop further comprising an error generating loop, the error generating loop providing an error output feedback when the information from the absolute pressure sensor indicates a low pressure level at which the system cannot operate. In the breastmilk expression system, a level setting loop may also be provided, the level setting loop determining and enabling available levels of operation of the system based on the information obtained from the absolute pressure sensor.

DETAILED DESCRIPTION OF THE PREFERRED EMBODIMENTS

Figure 1:
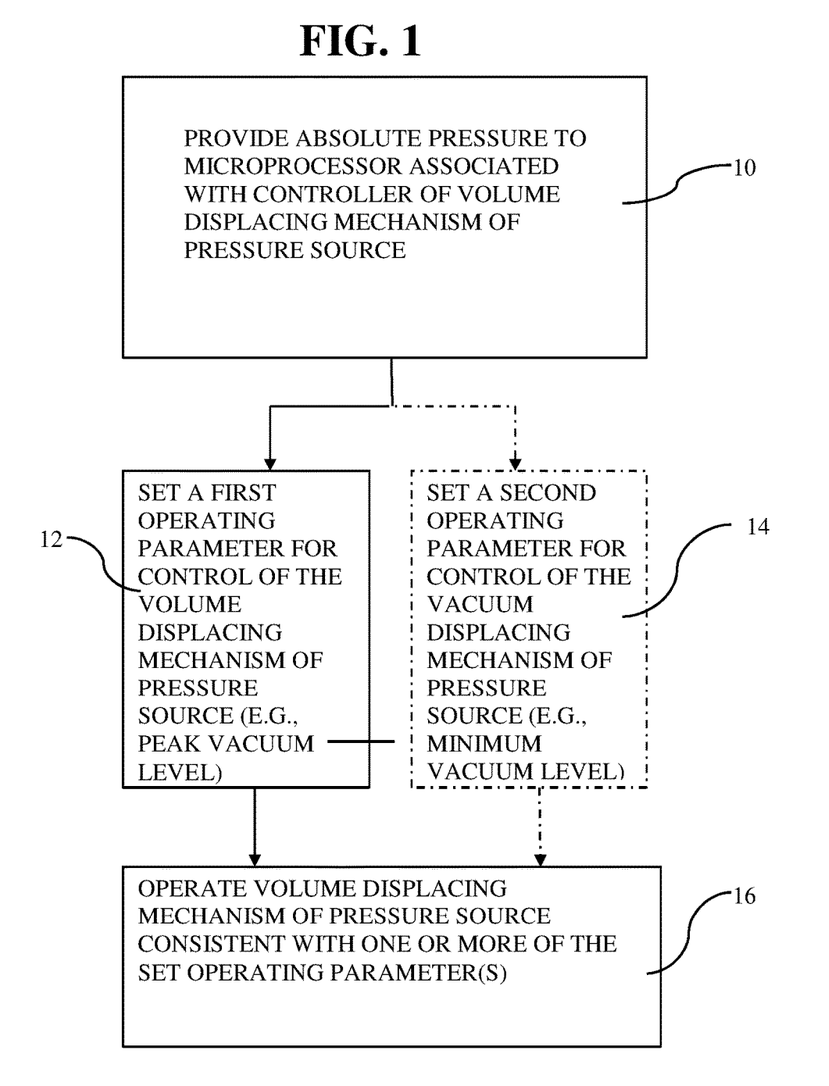
FIG. 1 is a flow diagram of steps in the operation of an exemplary pressure system of the present disclosure.
Figure 1A:
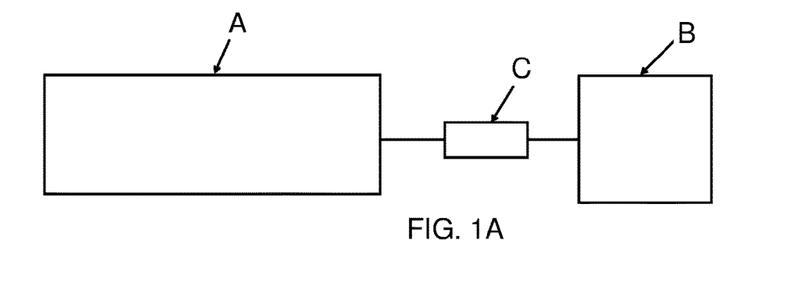
FIG. 1A is a schematic view of an exemplary pressure system constructed in accordance with the principles of the present disclosure.

As illustrated in FIG. 1A, an atmospheric pressure system constructed in accordance with the principles of the present disclosure can include a suitable pressure system A connected either directly or indirectly to an atmospheric pressure data source, such as an absolute pressure sensor C. A reading from the absolute pressure sensor C can be received by a controller B associated with and operably connected to the atmospheric pressure system. The controller B can then incorporate the reading from the absolute pressure sensor C into the operation of the pressure system A by either: 1) adjusting the range for a pressure cycle based on the information from the reading, or by 2) determining that the pressure system A cannot operate given the current reading of the absolute pressure sensor C. As a result, the system can operate using a single absolute pressure sensor and a circuit, rather than requiring both a differential pressure sensor and an absolute pressure sensor, or switch, to accomplish the same task, which reduces both the expense and the risk of failure for the device.

In another embodiment, the controller B can receive a reading from an absolute pressure sensor housed in a device associated with, or connectable to, the pressure system A. The reading can be transmitted to the controller in any suitable manner, such as by a hard wired connection, wireless signal, Bluetooth, or any other suitable transmission means.

In still another embodiment, atmospheric pressure data can be delivered to the controller B. Due to potential variations between stored atmospheric pressure data and an actual reading of measured atmospheric pressure using an absolute pressure sensor, the actual reading ensures reliability of the system under a wide range of weather and pressure conditions in a current environment of the device.

With reference to the exemplary embodiment of FIG. 1, a suitable pressure system, such as a breastmilk expression system, may be operated in accordance with the principles herein by a method that involves a number of steps. In a first step, an atmospheric pressure reading, or atmospheric pressure data, can be obtained. In a second step, the atmospheric pressure data from the reading can be received by a processor or microprocessor associated with or incorporated in a controller of the breastmilk expression system, as depicted by step-box 10.

Once the atmospheric pressure data has been obtained, an operating parameter decision for controlling the operation of the breastmilk expression system can be determined via associated or internal hardware or via the controller. The operating decision can result, for example, in carrying out an adjustment to the available pumping patterns given the available pressure conditions for the system, or any other suitable adjustment for a given pressure system.

Other operating decisions can be made based on the atmospheric information, or reading from the absolute pressure sensor. For example, the decision can be to provide an error message indicating that the breastmilk expression system cannot operate based on the reading received from the atmospheric pressure data. Although the same type of decisions could be determined in a system relying on stored atmospheric pressure data, the accuracy of operating devices using stored atmospheric pressure data depends on a present correlation between the data and true, measured atmospheric pressure sensor readings from a suitable device, such as an absolute pressure sensor. Where the present correlation does not exist, measured absolute pressure sensor readings are most reliable in accordance with the principles described herein.

Another exemplary embodiment of the pressure system can include an operating decision circuit for determining the available pressure ranges for the device in a particular location. In an embodiment of a breastpump system, the output of the operating decision circuit can be relied upon to update available breast pumping settings given an operating range for the device resulting from the atmospheric pressure data, as depicted by step-box 12. Other operating parameters can also be adjusted by operating decisions reached based on information from other sensors associated with the pressure system, if desired, as depicted by step-box 14.

In an embodiment, a circuit can be provided for processing the atmospheric pressure data to reach an operating decision. The circuit can include either hardware or software. The circuit can be operably connected to the controller. Alternatively, the circuit can include a separate processor. Optionally, in an embodiment the circuit further includes a memory and a controller in operable communication with an actuator, such as a motor, that drives a suitable pressure generating source of the pressure system. Once the operating decision(s) have been set, the pressure system can be operated in a manner consistent with the operating decision(s), as depicted by step-box 16. The operating decision may be carried out by a controller carrying out instructions provided by a software or firmware program. The program may be stored on a non-transitory computer readable medium, such as on a memory associated with the controller. In an embodiment the program may include instructions for generating one or more operating decisions for a pumping session of the breastmilk expression system based on the atmospheric pressure data.

Figure 2:
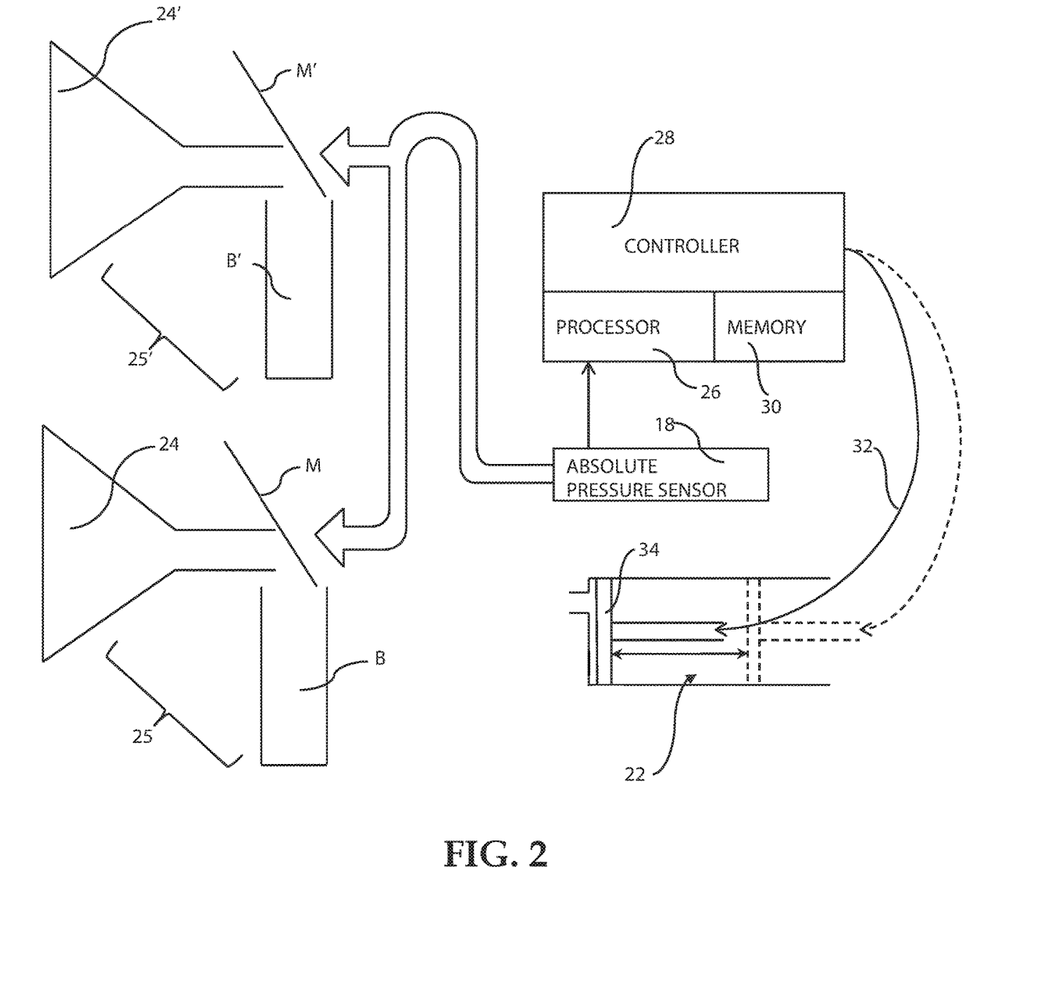
FIG. 2 is a semi-schematic diagram of various components of an exemplary pressure system of the present disclosure.

The atmospheric pressure data may be provided to the processor or microprocessor in step 10 in various ways. For instance, as illustrated in FIG. 2, an absolute pressure sensor 18 may enable collection of information including an absolute pressure reading from an absolute pressure sensor 18 or other suitable device, or data relating to a stored absolute pressure or other parameter. The information can be transmitted to a processor 26, which can be a microprocessor.

In an embodiment where the pressure system is a breastmilk expression system, the information can indicate an absolute pressure measured from an absolute pressure sensor disposed within a circuit 20 in fluid communication with both a pressure generator 22 and one or more components of the pressure system that cooperate with a breast-receiving member to apply pressure to the breast. For example, the breast-receiving member may be a breastshield 24 having a funnel shape, or any other suitable breast-receiving member. A second breastshield 24' can be provided to facilitate simultaneous expression of milk from both breasts during a single pumping session. Each of the breastshields 24, 24' can be part of a breastshield assembly 25, 25' that includes a breastmilk collection receptacle B, B', such as a bottle or a bag. For each of the two breastmilk collection kits, the breastmilk collection receptacle B, B' can be arranged in fluid communication with an aperture of the respective breastshield 24, 24' other than the breast-receiving opening of the breastshield 24, 24'.

In an embodiment, absolute pressure data indicative of environmental conditions is transmitted to the processor 26, as shown at step 10 of FIG. 1. The processor 26 can then process the absolute pressure sensor data through a hardwired or software circuit in order to set or adjust one or more operating parameters, such as peak vacuum level (step 12), minimum vacuum level (step 14), or the processor can create a feedback rule for available pressure levels determined in view of the environmental data from the absolute pressure data, or the processor can adjust any other pump parameter for which the environmental feedback information proves useful in optimizing the pressure system operation.

In an alternative embodiment, the processor 26 may interrogate a memory 30 associated therewith, which may be a non-volatile computer readable memory having data stored thereon and/or transmitted thereto with values that approximate data indicative of atmospheric pressure. Operating parameters can then be set or adjusted, such as one or more peak vacuum levels available, based on the stored or received data values. The processor 26 may execute an algorithm that calculates an appropriate value for operating parameters based on the environmental conditions reflected in the atmospheric pressure data. If desired, other variables can be supplied to the processor 26 to achieve optimum performance or any other desirable parameter.

In an embodiment, once the one or more operating decisions are set, a controller 28 associated with the processor 26 can signal an actuator 32 to activate a movable pressure generating member 34. In certain embodiments, the movable pressure generating member 34 can be disposed in a chamber of a pressure generating source, such as the vacuum source 22, or any other suitable pressure source. In an embodiment, the chamber can be in communication with the breastshield assembly 25, 25'.

In certain embodiments, an absolute pressure sensor can be positioned and connected to the pressure system to provide regular environmental condition information that can be used to continually or intermittently adjust various operating parameters, as desired. For example, the processor 26 can compare one or more data points obtained from the absolute pressure sensor 18 or derived from the absolute pressure sensor output during operation of the vacuum source 22. Further, the absolute pressure sensor data, or the reading from the absolute pressure sensor 18 can be incorporated into an algorithm adapted and configured to model plots of vacuum pressure-versus-time stored on a non-transitory computer readable medium, such as in the memory 30. In the event of a discrepancy between the measured vacuum and the model vacuum from the algorithm at a given time or over a given duration of time, the processor 26 may signal the controller 28 to adjust the system pressure 32 in an effort to counteract factors that may have caused or at least contributed to the discrepancy.

Further monitoring of the data transmitted from the absolute pressure sensor 18 to the processor 26 over time can help determine whether remedial steps taken to correct a vacuum level during operation were adequate in view of the environmental conditions. Alternatively, a relative pressure level can be calculated based on the absolute pressure sensor data, and used to generate a model curve or plot of vacuum pressure-versus-time for a given session of operation of the pressure system.

Figure 3:
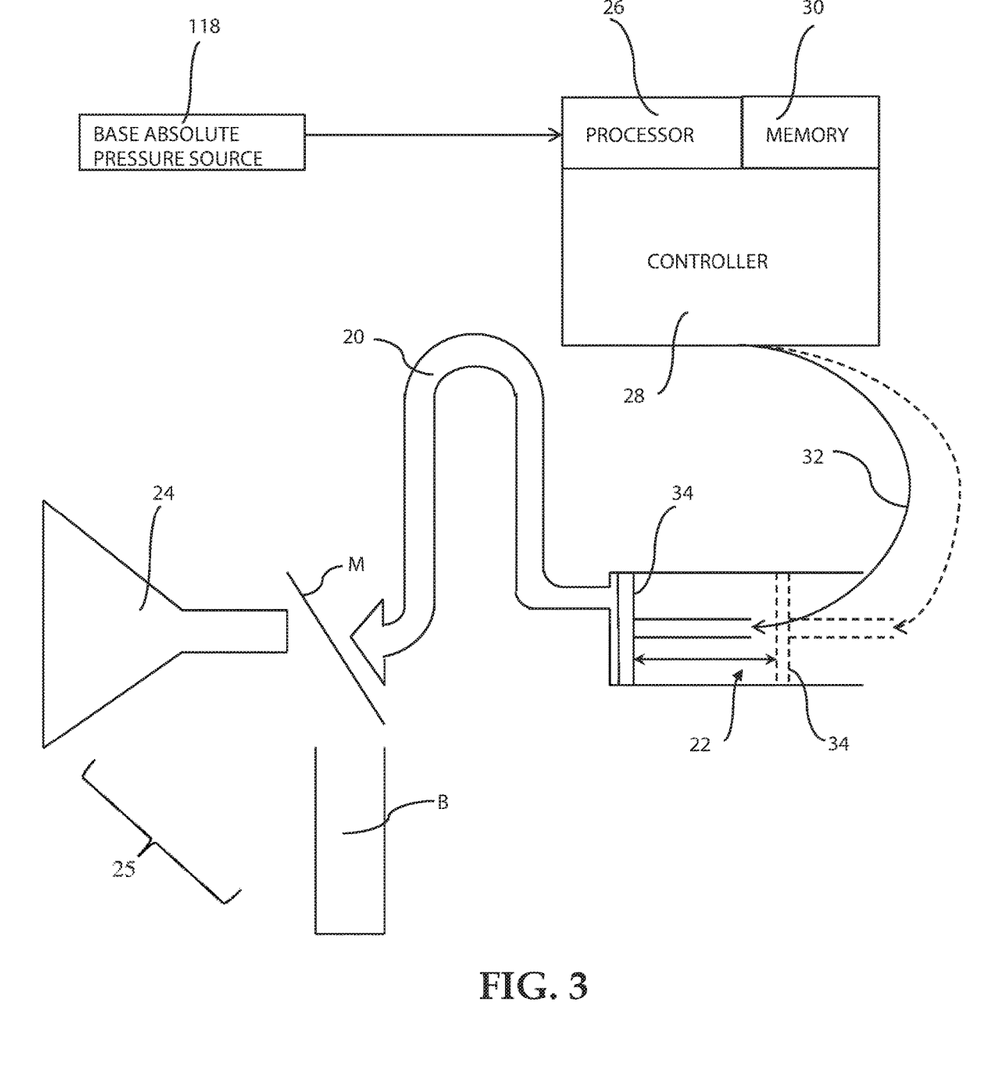
FIG. 3 is a semi-schematic diagram of various components of a pressure system of an alternate embodiment of the present disclosure.

As illustrated in the exemplary embodiment of FIG. 3, a device of the present disclosure is illustrated, semi-schematically, wherein the source of data indicative of atmospheric pressure is outside of the circuit 20. For instance, the source of data may be an atmospheric pressure source 118 in the form of a barometer or other indicator of atmospheric pressure. If the pressure circuit 20 is vented to ambient air before the pressure system is actuated, then the absolute pressure of the pressure circuit 20 starts at atmospheric pressure.

A user may provide the processor 26 with a location, such as by entering location data into a user interface, and the processor 26 compares the location data to location data stored on a non-transitory computer readable medium such as in the memory 30. The memory 30 may provide the processor 26 with data indicative of average atmospheric pressure for the location identified by the location data. The processor 26 may in turn use that atmospheric pressure data to calculate one or more operation parameters for the vacuum source 22. It will be appreciated that the memory 30 may be provided with data indicative of one or more operating parameters correlated to the location data, and for purposes of the present disclosure and appended claims, such a conversion of location data to atmospheric pressure data for consideration of one or more operating parameters is considered setting one or more operating parameters based on atmospheric pressure data provided to the processor.

Figure 4:
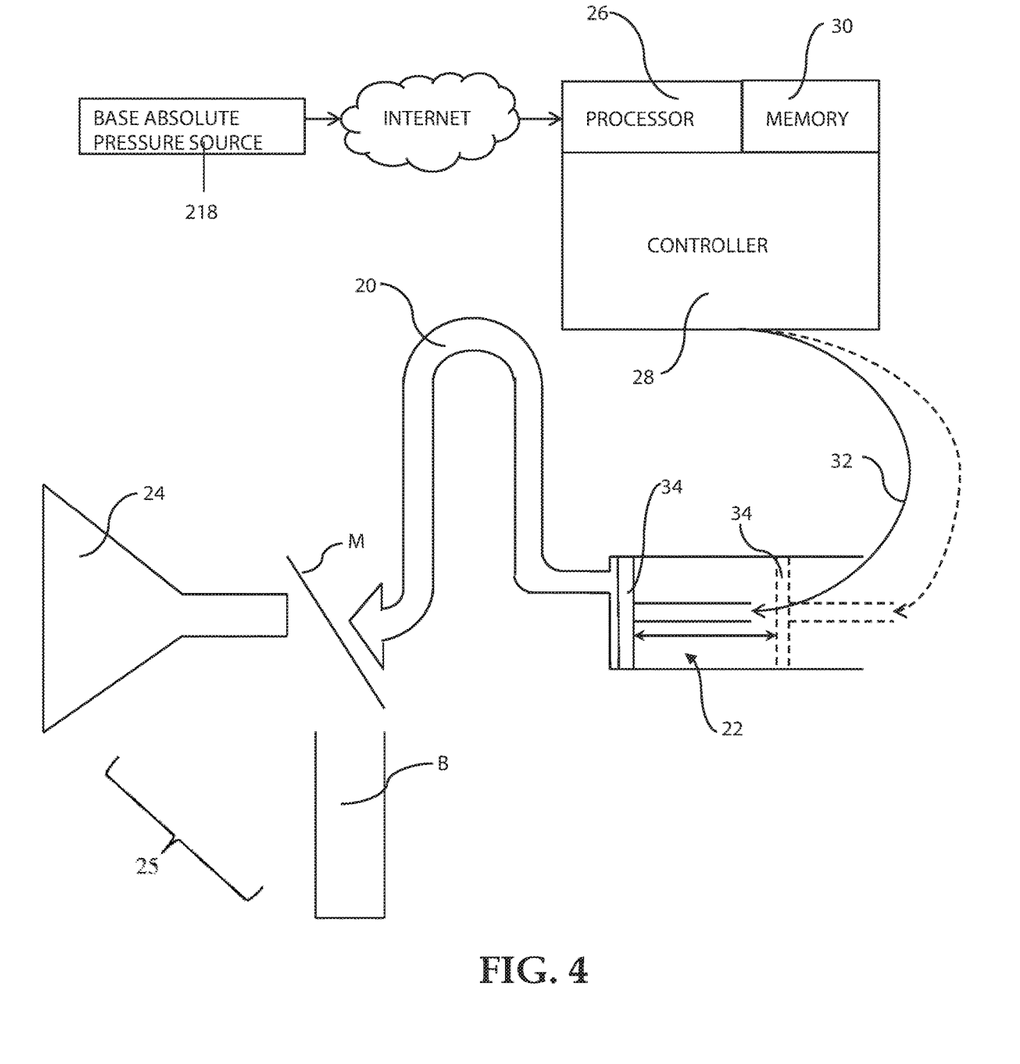
FIG. 4 is a semi-schematic diagram of various components of a pressure system of another alternate embodiment of the present disclosure.

As illustrated in FIG. 4, the source 218 of atmospheric pressure data may be located remotely from the pressure system. For example, the processor 26 may communicate with a software application installed on the memory 30 or installed on a smartphone, notebook computer, tablet, phablet, GPS (Global Positioning System) or GPS-enabled device, printer, smart watch, smart glasses, smart bracelet, wearable electronic device, PDA (personal digital assistant), pager, computing device configured for wireless communication, or the like (not shown) that is connected wirelessly or via a data cord or some combination thereof to the processor 26. The software application may be programmed to retrieve, via an internet connection, telephonic data communication, satellite transmission, cable television transmission, or some combination thereof, data indicative of atmospheric pressure, or average ambient pressure, at the location of the pressure system.

According to an embodiment, a pressure system is provided. The pressure system may comprise a pressure circuit selectively connected to the pressure system, an atmospheric pressure element in communication with the pressure circuit of the pressure system, and one or more operating parameters for the pressure system being controllable based on a circuit that limits operation based on a reading from the atmospheric pressure element that is received by the pressure circuit.

In an aspect, the pressure system may further comprise a pressure source, the pressure circuit connecting the pressure source to a breastshield assembly of the pressure system.

In an aspect, the pressure source may be a positive pressure source or a negative pressure source.

In an aspect, the pressure system may further comprise a circuit for setting a peak negative pressure based on the reading.

In an aspect, the atmospheric pressure element may comprise an absolute pressure sensor connected at least one of directly and indirectly to the pressure circuit.

In another embodiment, a pressure system is provided. The pressure system may comprise a system for at least one of establishing, controlling, and retrieving one or more operating parameters for the pressure system based on atmospheric pressure data for the pressure system, including, a pressure source that selectively exposes the pressure system to ambient air, and an absolute pressure sensor connected to the pressure system, the absolute pressure sensor forming a data sensing communication loop with a controller of the pressure source through which absolute pressure data transmits to the controller.

In an aspect, the controller may include a program stored on a non-transitory computer readable medium, the program including instructions responsive to the absolute pressure data.

In an aspect, the pressure system may be further defined by a breastmilk expression system wherein the pressure source includes a reciprocating volume displacing mechanism.

In an aspect, the pressure system may further comprise a chamber for housing the reciprocating volume displacing mechanism, an interior of the chamber in communication with a breastshield assembly.

In another embodiment, a method of manufacturing a pressure system is provided. The method may include providing an atmospheric pressure data source connectable to a pressure circuit of the pressure system; and providing a processor in operable communication with the pressure system, the processor configured to receive atmospheric pressure data from the atmospheric pressure data source.

In an aspect, the processor may be further configured to determine a peak pressure level for operating the pressure system using the atmospheric pressure data.

In an aspect, the atmospheric pressure data may be obtained repeatedly for the pressure system via an absolute pressure sensor.

In an aspect, the pressure system may be configured to deliver a non-uniform pressure curve during a cycle.

In another embodiment, a method for initializing a pressure source of a breastmilk expression system is provided. The method may include selectively placing a pneumatic circuit of the breastmilk expression system in communication with ambient air; identifying atmospheric pressure within the pneumatic circuit of the breastmilk expression system; and setting a peak available pressure based on the identified atmospheric pressure.

In an aspect, identifying the atmospheric pressure within the pneumatic circuit of the breastmilk expression system may include measuring absolute pressure using an absolute pressure sensor.

In another embodiment, a breastmilk expression system may be provided. The breastmilk expression system may include a pressure source; a breastshield assembly in fluid communication with the pressure source; and an absolute pressure sensor in fluid communication with the pressure source and the breastshield assembly, the absolute pressure sensor being in selective communication with an outlet exposing the absolute pressure sensor to ambient pressure.

In an aspect, the breastmilk expression system may further include an operating parameter decision loop, operably connected to the absolute pressure sensor, and configured to control an operation of the breastmilk expression system based on information obtained from the absolute pressure sensor.

In an aspect, the operating parameter decision loop may include an error generating loop, the error generating loop providing an error output feedback when the information from the absolute pressure sensor indicates a low pressure level at which the system cannot operate.

In an aspect, the breastmilk expression system may further include a level setting loop, the level setting loop determining and enabling available levels of operation of the breastmilk expression system based on the information obtained from the absolute pressure sensor.

While various embodiments have been described above, it will be appreciated that variations may be made thereto that are still within the scope of the appended claims.

What is claimed is:

1. A breastmilk expression system comprising:
   a pressure circuit;
   a breastshield component in communication with the pressure circuit to apply pressure to a breast of a user;
   a user interface;
   a pressure source connected to the pressure circuit and comprising a volume displacing mechanism; and
   a controller in communication with the pressure source and the user interface, and configured to:
   receive, via the user interface, location data identifying a location,
   determine an atmospheric pressure associated with the location identified by the location data,
   determine, based on the atmospheric pressure, (i) a minimum vacuum level for operating the breastmilk expression system, and (ii) a peak vacuum level for operating the breastmilk expression system,
   set the peak vacuum level,
   set the minimum vacuum level, and
   control a displacement of the volume displacing mechanism to cause the breastshield component to adjust the pressure applied by the breastshield component to the breast of the user to be within the minimum vacuum level and the peak vacuum level.

2. The breastmilk expression system of claim 1, wherein the pressure source is a positive pressure source or a negative pressure source.

3. The breastmilk expression system of claim 1, further comprising:
an atmospheric pressure element exposed to ambient air.

4. A method for operating a breastmilk expression system, the method comprising:
providing the breastmilk expression system comprising:
a pressure circuit,
a breastshield component in communication with the pressure circuit to apply pressure to a breast of a user,
a user interface, and
a pressure source connected to the pressure circuit and comprising a volume displacing mechanism;
receiving, via the user interface, location data identifying a location;
determining an atmospheric pressure associated with the location identified by the location data;
determining, by a controller in communication with the user interface and the pressure source, and based on the atmospheric pressure, (i) a minimum vacuum level for operating the breastmilk expression system, and (ii) a peak vacuum level for operating the breastmilk expression system;
setting, by the controller, the peak vacuum level;
setting, by the controller, the minimum vacuum level; and
controlling, by the controller, a displacement of the volume displacing mechanism to cause the breastshield component to adjust the pressure applied by the breastshield component to the breast of the user to be within the minimum vacuum level and the peak vacuum level.

5. The method of claim 4, wherein the pressure source is a positive pressure source or a negative pressure source.

6. The method of claim 4, wherein providing the breastmilk expression system further comprises an atmospheric pressure element exposed to ambient air.

* * * * *